United States Patent [19]

Edington et al.

[11] 4,272,628
[45] Jun. 9, 1981

[54] NOVEL PYRIDINE DERIVATIVES

[75] Inventors: Edwin T. Edington, Cookham; Alan C. White, Windsor, both of England

[73] Assignee: John Wyeth & Brother Limited, Maidhead, England

[21] Appl. No.: 51,077

[22] Filed: Jun. 22, 1979

Related U.S. Application Data

[63] Continuation-in-part of Ser. No. 873,192, Jan. 30, 1978, Pat. No. 4,180,670.

[30] Foreign Application Priority Data

Feb. 2, 1977 [GB] United Kingdom ................. 4354/77
Jul. 9, 1977 [GB] United Kingdom ............... 28879/77

[51] Int. Cl.³ .......................................... C07D 213/32
[52] U.S. Cl. ................................... 546/284; 424/263; 546/257; 546/270; 546/304
[58] Field of Search ............... 546/284, 304, 257, 270; 549/81

[56] References Cited

U.S. PATENT DOCUMENTS 2,713,048  7/1955  Weston ................................ 546/284
4,180,670  12/1979 Edington ............................. 260/284

OTHER PUBLICATIONS

Orcutt et al., Chem. Abst. vol. 44, col. 10156 (1950).
Huttrer et al., J. Am. Chem. Soc. 1999-2002 (1946).
Wade, Martindale The Extra Pharmacopoedia, pp. 1287-1309 (1977).
Carpendo et al., Chem. Abst. 73, abst, 108,061 (1970).
Kyrides et al, J. Am. Chem. Soc. vol. 72, pp. 745-748 (1950).
Vilani et al., J. Am. Chem. Soc. vol. 73, pp. 5916-5917 (1951).
Jain et al., J. Med. Chem. vol. 11, pp. 87-92 (1968).
Kato et al., Chemical Abstracts, vol. 46, abst. 4541a to d (1952).

Primary Examiner—John D. Randolph
Attorney, Agent, or Firm—Arthur E. Wilfond

[57] ABSTRACT

New 4-pyridinamine derivatives having the formula

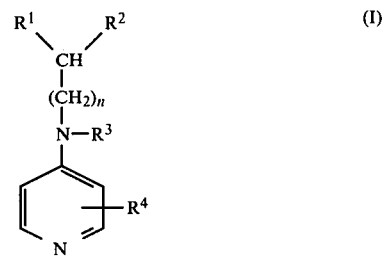

and their pharmaceutically acceptable acid addition salts, [wherein one of $R^1$ and $R^2$ is aryl or heteroaryl, the other of $R^1$ and $R^2$ is lower alkyl, $R^3$ and $R^4$ are independently hydrogen or lower alkyl, and n is 0 or 1] are described. They show CNS activity and may used as antidepressant drugs. N-([α-Phenyl]-n-propyl)-4-pyridinamine also shows anti-ulcer activity.

5 Claims, No Drawings

NOVEL PYRIDINE DERIVATIVES

This is a continuation-in-part of our U.S. Pat. application Ser. No. 873,192 filed Jan. 30, 1978, now U.S. Pat. No. 4,180,670, entitled "Amino Pyridine Derivatives".

The invention relates to novel pyridine derivatives which show pharmaceutical activity, particularly CNS activity. The invention provides the pyridine derivatives and pharmaceutical compositions containing them.

The invention provides novel pyridine derivatives having the formula

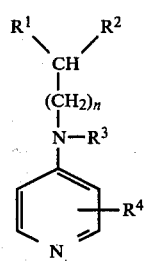

and their pharmaceutically acceptable acid addition salts, wherein one of $R^1$ and $R^2$ represents aryl or heteroaryl, the other of $R^1$ and $R^2$ represents lower alkyl, $R^3$ and $R^4$ are independently selected from hydrogen and lower alkyl and n represents 0 to 1.

By the term "lower" as used herein in connection with such groups as alkyl, alkylene and alkoxy, there is meant that the group contains up to 6 carbon atoms, preferably up to 4 carbon atoms. By the term "aryl or heteroaryl" there is meant a monovalent group having aromatic character. As examples of such a group representing one of $R^1$ and $R^2$ there may be mentioned phenyl; naphthyl; phenyl substituted by one to two substituents selected from halogen, lower alkyl, lower alkoxy, lower alkylenedioxy and trifluoromethyl; thienyl and pyridyl.

The other of $R^1$ and $R^2$ represents lower alkyl, for example, methyl, ethyl, propyl and butyl. $R^3$ and $R^4$ may be the same or different and are selected from hydrogen and lower alkyl, for example, methyl, ethyl, propyl and butyl. $R^3$ and $R^4$ are preferably chosen from hydrogen and methyl. The symbol n selected from 0 to 1 and is preferably 0.

A preferred class of compounds according to the invention are those having formula I where one of $R^1$ and $R^2$ is phenyl or thienyl, the other of $R^1$ and $R^2$ is $C_2$ to $C_4$ alkyl, $R^3$ and $R^4$ are hydrogen and n is 0 and their pharmaceutically acceptable acid addition salts.

The invention may be particularly exemplified by N-([α-phenyl]-n-propyl)-4-pyridinamine, N-([α-phenyl]-n-pentyl)-4-pyridinamine, N-[α-butyl-2-thenyl]-4-pyridinamine and their pharmaceutically acceptable acid addition salts.

It will be apparent to the reader that the compounds of the invention possess an asymmetric carbon atom and thus exhibit the property of optical isomerism. The invention includes the individual optical isomers as well as the racemic mixtures. The racemates may be resolved into individual optical isomers in known manner.

The compounds of general formula I and their acid addition salts can be prepared in a number of ways by building up the molecule from suitable starting materials in known manner. A choice of methods exists so that the most appropriate one may be chosen in each case. In particular the compounds may be prepared by reduction of amides, conversion of primary amines into secondary amines or conversion of secondary amines into tertiary amines, by reaction of an organometallic compound with Schiff's bases, and by reduction of Schiff's bases.

The invention provides a process for the preparation of a compound having formula I or a pharmaceutically acceptable acid addition salt thereof, wherein (a) a compound having the formula III

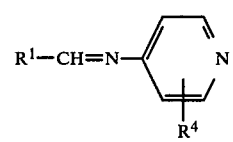

(where $R^1$ and $R^4$ are as defined above) is treated with a reactive organometallic compound whose organo moiety is $R^2$ as defined above; or (b) an amine having the formula IV

or a salt thereof, is reacted with a compound having formula VIII

(where Z is a replaceable atom or group) to form an amine having the formula IX

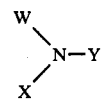

as a free base or acid addition salt (where in formulae IV, V and VI any one of W, X and Y represents a group having the formula

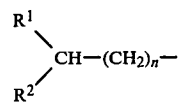

(where $R^1$, $R^2$ and n are as defined above), another one of W, X and Y represents a group having the formula

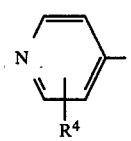

(where $R^4$ is as defined above) and the remaining one of W, X and Y represents $R^3$ as defined above subject to the proviso that, when Y represents $R^3$ as defined above, then $R^3$ is lower alkyl); or (c) a Schiff's base having the formula IX or X

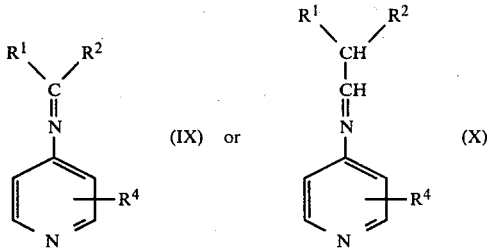

(wherein $R^1$, $R^2$ and $R^4$ are as defined above) is reduced; or (d) an amide having the formula XI

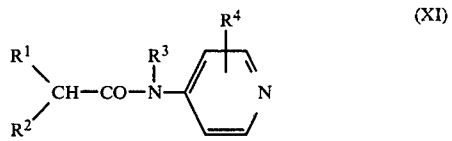

or an acid addition salt thereof (wherein $R^1$, $R^2$, $R^3$ and $R^4$ are as defined above) is reduced to form a compound where n is 1. Where desired, the process may include conversion of a free base form of the compound having formula I into a pharmaceutically acceptable acid addition salt thereof or conversion of an acid addition salt form of a compound having formula I into its base form.

The starting materials for methods (a) and (b) namely those having formula III, IV and V, and the reactive organometallic compound are sometimes known and, where new, can be prepared in known manner. The compounds having general formula XI and their acid addition salts are new compounds. They can be prepared in manner known per se. In particular an amine having the formula

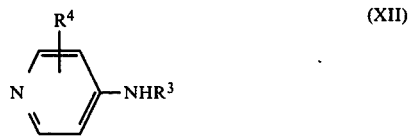

(where $R^3$ and $R^4$ are as defined above) is acylated to introduce the acyl group

(where $R^1$ and $R^2$ are as defined above).

The acylation may be performed using the acyl halide, for instance, the acyl chloride or acyl bromide, in the presence of a suitable base. The Schiff's bases of formulae IX and X are obtainable in known manner.

The compounds having the formula III are Schiff's bases which can be prepared in known manner by condensation of an aldehyde of formula $R^1CHO$ with 4-pyridinamine or a 2- or 3-(lower alkyl) derivative thereof. Method (a) is preferably carried out by using a compound having the formula $R^2Li$ as the organometallic compound. Alternatively a Grignard reagent such as lower alkyl magnesium bromide may be employed.

The reaction is preferably carried out in an inert solvent such as ether under an inert atmosphere such as nitrogen. The reaction yields an amine having the formula XIV

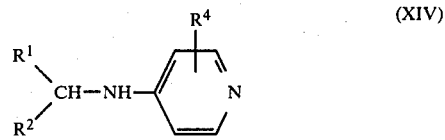

in the form of a salt such as the lithium salt. Decomposition of the resulting reaction complex with ice water or a cold solution of ammonium chloride gives the amine which can be recovered in standard manner.

Method (b) can be carried out using known procedures for converting primary amines into secondary amines and secondary amines into tertiary amines. We prefer to use a compound of formula V in which Z is halogen, particularly bromine or chlorine.

The starting amine may be used as such or in the form of a salt thereof, for instance, the lithium salt. An example of the use of the salt is as follows: An organometallic compound such as the lithium salt having the formula $R^2Li$ is reacted with a Schiff's base having formula III to give a compound having the formula XIV in the form of its lithium salt having the formula XV

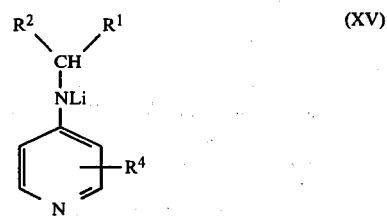

This procedure may be carried out as described under method (a). However instead of treating the salt with water as in method (a) the lithium salt is treated with a lower alkyl halide, for example, methyl chloride or ethyl bromide, to effect alkylation to result in a tertiary amine in which $R^3$ is lower alkyl.

Method (b) may also be used to form secondary amines. For example a compound having the formula $$W-NH_2$$

may be treated with a compound having formula Y—Z (where one of W and Y represents a group having the formula VII and the other represents a group having formula VIII to form a secondary amine of formula W—NH—Y. We prefer to carry out this method by reacting an appropriately substituted methyl halide of formula XVI

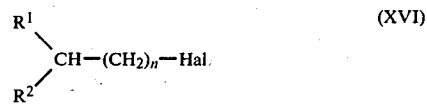

(where Hal is halogen such as chlorine or bromine and n is 0 or 1) with an amine having the formula XIV.

The reaction of the amine having formula IV with the compound having formula V may be carried out under elevated temperature in a suitable solvent, for example, toluene.

The reduction according to method (c) may be carried out under conditions known for the reduction of Schiff's bases to form amines. As reducing agent there may be used lithium aluminium hydride or sodium borohydride. In particular, the reduction may be performed using sodium borohydride in an alcohol, for instance, methanol or ethanol, at room temperature. The reduction may also be carried out using lithium aluminium hydride in ether at room temperature or under reflux. Catalytic hydrogenation may be used. The reduction conditions employed should be so chosen as to avoid reduction of the pyridine ring and/or cleavage of the group —$CHR^1R^2$.

It will be appreciated that the reduction products obtained from Schiff's bases of formula IX are compounds where n is 0 and $R^3$ is hydrogen and those obtained from Schiff's bases of formula X are compounds where n is 1 and $R^3$ is hydrogen.

The reduction according to method (d) may be carried out under conditions known for the reduction of amides to form amines. As reducing agent there may be used lithium aluminium hydride or diborane. It will be appreciated that the reduction products obtained are compounds where n is 1.

When a product of formula I has been prepared in the form of its free base this may be converted into an acid addition salt by addition of an acid. For example, ethereal hydrogen bromide or ethereal hydrogen chloride may be added to a solution of the free base to give the hydrobromide or hydrochloride salt respectively. Acid addition salt forms of compounds having formula II may be converted into the free base form in known manner, in particular, by addition of a base.

The compounds having formula I and their pharmaceutically acceptable acid addition salts are indicated for pharmaceutical use. In particular they show CNS (central nervous system) activity, when tested on warm blooded animals. They reverse the hypothermia induced by reserpine on mice and thus may have potential use as antidepressant drugs. N-([α-Phenyl]-n-propyl)-4-pyridinamine and its acid addition salts also show anti-ulcer activity. Anti-ulcer activity may be determined according to the method of Senay and Levine, Proc. Soc. Exp. Biol. Med., 124, 1221–3 (1967).

The reserpine hypothermia test can be carried out by the following procedure:

Groups of 10 female mice (21 to 25 g) are dosed with reserpine, 2.5 mg/kg s.c. The mice are placed in cages without sawdust but with food and water at 18° C. After 17 hours (overnight) the rectal temperature of each mouse is measured with a thermocouple inserted to a standard depth of 2 cm. The mice are then challenged with compounds at graded dose levels either orally or intraperitoneally. The rectal temperature is measured hourly for six hours or until a maximum rise in temperature is achieved whichever is the shorter. A control group is run. The rise in rectal temperature caused by the drug is compared with that in the control group.

In this procedure the compound of Example 2 was active at 10 mg/kg p.o. and the compound of Example 3 was active at 5 mg/kg p.o.

The invention also includes pharmaceutical compositions containing as active ingredient a compound of formula I or a pharmaceutically acceptable acid addition salt thereof which may be micronised if desired. In addition to the active ingredient said compositions also contain a pharmaceutically acceptable carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80%, by weight of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formulation of an active ingredient with an encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, a sterile organic solvent or a mixture of both. Preferably a liquid carrier is one suitable for parenteral injection. Where the active ingredient is sufficiently soluble it can be dissolved in a suitable organic solvent, for instance aqueous propylene glycol or polyethylene glycol solutions. Aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilised by intramuscular, intraperitoneal or subcutaneous injection. In many instances a compound is orally active and can be administered orally either in liquid or solid composition form.

Preferably the pharmaceutical composition is in unit dosage form. In such form, the composition is subdivided in unit doses containing appropriate quantities of the active ingredient; the unit dosage form can be a packaged composition, the package containing specific quantities of compositions, for example, packeted powders or vials or ampoules. The unit dosage form can be a capsule, cachet or tablet itself, or it can be the appropriate number of any of these in package form. The quantity of active ingredients in a unit dose of composition may be varied or adjusted from 5 mg or less to 500 or more, according to the particular need and the activity of the active ingredient. The invention also includes the compounds in the absence of carrier where the compounds are in unit dosage form.

The following Examples illustrate the invention:

EXAMPLE 1

N-[α-butyl-2-thenyl]-4-pyridinamine

To a stirred, cooled (10°–20° C.) solution of 3,77 grams of 4-(2-thenylideneamino)pyridine in 100 milliliters of dry ether, a solution containing 0.025 mole butyl lithium in 50 milliliters of dry ether was added dropwise. The resulting solution was stirred at room temperature for 4 hours, and then diluted with 150 ml dry ether before cautious addition of 50 ml. water. The organic phase was dried (MgSO$_4$) and evaporated to dryness to give 5.24 grams of a brown oil. This brown oil was dissolved in toluene and extracted with 2N hydrochloric acid. The extracts were basified with sodium hydroxide and extracted back into toluene. The resulting solution of the base in toluene was dried (MgSO$_4$) and evaporated to dryness. The resulting oil was crystallised from petrol (100°–120° C.)/toluene affording 2.0 grams of a white solid. This material was dissolved in isopropanol and converted to the hydrochloride salt with ethereal hydrogen chloride and crystallised by addition of ether, yielding 1.153 grams of N-[α-butyl-2-thenyl]-4-pyridinamine hydrochloride of melting point 146.5°–148° C.

Analysis: Found C, 59.27%; H, 6.95%; N, 9.93%. C$_{14}$H$_{18}$N$_2$.HCl requires C, 59.45%; H, 6.77%; N, 9.90%

EXAMPLE 2

N-([α-phenyl]-n-pentyl)-4-pyridinamine 0.03 Mole of butyl lithium in hexane as a 15% w/w solution was added dropwise to a stirred, cooled (−10° C.) solution of 5.46 grams (0.03 mole) of 4-benzylideneamino pyridine in 10 milliliters of dry ether. The mixture was allowed to warm to room temperature and then poured onto ice and extracted with methylene chloride. The organic phase was separated and extracted with 2 N hydrochloric acid. The extracts were basified with 2 N sodium hydroxide and extracted into methylene chloride. The resulting methylene chloride solution was dried (MgSO$_4$) and decolourised with charcoal. The solvent was removed and the resulting light oil (5.75 grams) was crystallised and recrystallised from a toluene/petrol 60°–80° C.) mixture affording 2.36 grams of N-([α-phenyl]-n-pentyl)-4-pyridinamine, melting point 118°–8.5°.

Analysis: Found: C, 79.94%; H, 8.40%; N, 11.58%. C$_{16}$H$_{20}$N$_2$ requires C, 79.97%; H, 8.39%; N, 11.66%.

The hydrochloride salt was prepared by dissolving the base in 2-propanol and treating with a solution of hydrogen chloride in dry ether. The salt had a melting point of 155.5°–157° C.

Analysis: Found: C, 69.13%; H, 7.60%; N, 10.03%. C$_{16}$H$_{21}$N$_2$Cl required C, 69.43%; H, 7.65%; N, 10.12%.

EXAMPLE 3

N-([α-phenyl]-n-propyl)-4-pyridinamine 5.4 Grams (0.03 mole) of 4-(benzylidineamino) pyridine in 20 milliliters of dry ether was added to a stirred solution of ethyl lithium (from 3.6 grams ethyl bromide and 0.42 grams of lithium) in 50 milliliters of ether under a nitrogen atmosphere at −10° C. The reaction mixture was allowed to warm to room temperature and after 1 hour decomposed by the addition of water. A solid precipitated and was dissolved by adding toluene. The organic phase was separated and the basic material was extracted with 2N hydrochloric acid. The acid extracts were basified with 5N sodium hydroxide solution and extracted into toluene. The toluene extracts were dried (MgSO$_4$) and the solvent was evaporated. The oil which remained was crystallised from a mixture of toluene and light petroleum (boiling point 60°–80° C.) to afford 3.43 grams of white crystals of the title compound, melting point 112° to 114° C.

Analysis: Found: C, 79.2%; H, 7.6%; N, 13.3%. C$_{14}$H$_{16}$N$_2$ requires C, 79.21%; H, 7.6%; N, 13.2%.

A solution of the base in hot isopropanol was treated with hydrogen bromide in ether to give 3.33 grams of the title compound as its hydrobromide salt, melting point 190°–192° C.

EXAMPLE IV

The following alkyl lithium compounds are reacted with the following Schiff's bases in a manner similar to Examples 1 to 3 to form the following products:

| Alkyl lithium | Schiff's Base | Product |
| --- | --- | --- |
| Methyl lithium | 2-Methyl-4-(2-thenylidene amino)pyridine | 2-Methyl-N-[α-methyl-2-thenyl]-4-pyridinamine |
| Ethyl lithium | 4-(p-Ethoxybenzylidene-amino)pyridine | N-[α-(p-Ethoxyphenyl)-n-propyl]-4-pyridinamine |
| Butyl lithium | 4-(3,4-methylenedioxy benzylideneamino)pyridine | N-[α-(3,4-Methylene-dioxyphenyl)-n-pentyl]-4-pyridinamine |
| Isopropyl lithium | 4-(2-Pyridylmethylene-amino)pyridine | N-[α-(2-Pyridyl)-isobutyl]-4-pyridinamine |
| Propyl lithium | 4-(o-Methylbenzylidene-amino)pyridine | N-[α-(o-Tolyl)-n-butyl]-4-pyridinamine |
| Pentyl lithium | 4-(p-Bromobenzylidene-amino)pyridine | N-[α-(p-Bromophenyl)-n-hexyl]-4-pyridinamine |
| Butyl lithium | 4-(1-Naphthylmethylene-amino)pyridine | N-[α-(1-Naphthyl)-n-pentyl]-4-pyridinamine |
| Ethyl lithium | 4-(3,5-Dichlorobenzyl-ideneamino)pyridine | N-[α-(3,5-Dichloro-phenyl)-n-propyl]-4-pyridinamine |
| Butyl lithium | 4-(m-Trifluoromethyl-benzylideneamino)pyridine | N-[α-(Trifluoromethyl-phenyl)-n-pentyl]-4-pyridinamine |

EXAMPLE 5

N-Methyl-N-([α-phenyl]-n-propyl)-4-Pyridinamine

A solution of 0.01 mole of N-([α-phenyl]-n-propyl)-4-pyridinamine in 100 milliliters of dry tetrahydrofuran is added at −10° C. to a solution of lithium diisopropylamide (prepared from 1.5 milliliters of diisopropylamine and butyl lithium in hexane at −20° C.) in 100 milliliters of tetrahydrofuran, in an atmosphere of nitrogen. The solution is stirred at room temperature for 30 minutes and then treated with 0.63 milliliters of methyl iodide and stirred at room temperature overnight. The solution is decomposed with 5 milliliters of water. The solution is evaporated and the residue is dissolved in propan-2-ol. Acidification with ethereal hydrogen chloride is followed by careful addition of ether to give the title compound in the form of the hydrochloride.

EXAMPLE VI

N-[(β-phenyl)-n-propyl]-4-pyridinamine

β-(phenyl)-N-(4-pyridyl)propionamide is prepared by reacting 4-aminopyridine with β-(phenyl)propionyl chloride in pyridine at room temperature. The amide is reduced to give the title compound by treating a solution of the amide in dry tetrahydrofuran stirred and cooled to 0° C. with diborane in a stream of nitrogen.

We claim:

1. A compound selected from those having the formula

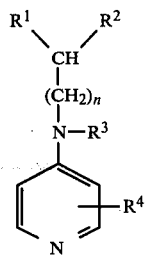 (I)

and their pharmaceutically acceptable acid addition salts, wherein one of $R^1$ and $R^2$ is phenyl; naphthyl; phenyl substituted by one to two substituents selected from halogen, lower alkyl, lower alkoxy, lower alkylenedioxy and trifluoromethyl; thienyl and pyridyl, the other of $R^1$ and $R^2$ is lower alkyl, $R^3$ and $R^4$ are independently selected from hydrogen and lower alkyl and n is selected from 0 and 1.

2. A compound as defined in claim 1, where n is 0.

3. A compound as defined in claim 1, which is N-[(α-phenyl)-n-propyl]-4-pyridinamine or a pharmaceutically acceptable acid addition salt thereof.

4. A compound as defined in claim 1, which is N-[(α-phenyl)-n-pentyl]-4-pyridinamine or a pharmaceutically acceptable acid addition salt thereof.

5. A compound as defined in claim 1 which is N-[α-butyl-2-thenyl]-4-pyridinamine or a pharmaceutically acceptable acid addition salt thereof.

* * * * *